(12) United States Patent
Moore (10) Patent No.: US 11,786,421 B2
(45) Date of Patent: Oct. 17, 2023

(54) WHEELCHAIR SYSTEMS WITH EMERGENCY STOP FEATURES

(71) Applicant: Toyota Motor North America, Inc., Plano, TX (US)

(72) Inventor: Douglas A. Moore, Fairview, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 523 days.

(21) Appl. No.: 17/022,657

(22) Filed: Sep. 16, 2020

(65) Prior Publication Data

US 2022/0079822 A1    Mar. 17, 2022

(51) Int. Cl.
*A61G 5/10* (2006.01)
*A61G 5/04* (2013.01)

(52) U.S. Cl.
CPC .............. *A61G 5/1005* (2013.01); *A61G 5/04* (2013.01); *A61G 5/1075* (2013.01); *A61G 2203/36* (2013.01)

(58) Field of Classification Search
CPC .................................................. A61G 5/1005
See application file for complete search history.

(56) References Cited

U.S. PATENT DOCUMENTS

| | | | |
|---|---|---|---|
| 6,068,280 A | 5/2000 | Torres | |
| 6,392,556 B2 | 5/2002 | Tomich | |
| 7,144,025 B2* | 12/2006 | Wakita | A61G 5/1016 188/72.1 |
| 9,862,603 B1* | 1/2018 | Cochran | C01B 11/022 |
| 9,959,733 B2 | 5/2018 | Gu et al. | |
| 10,039,682 B2* | 8/2018 | Einav | G16H 20/30 |
| 10,172,752 B2 | 1/2019 | Goffer | |
| 11,369,309 B2* | 6/2022 | Larson | A61B 5/447 |
| 11,382,809 B2* | 7/2022 | Peskin | A61G 5/047 |
| 2001/0001237 A1* | 5/2001 | Stroda | A61B 5/1117 600/595 |
| 2005/0087954 A1 | 4/2005 | Wakita et al. | |
| 2015/0209207 A1 | 7/2015 | Cooper et al. | |
| 2021/0142643 A1* | 5/2021 | Susna | A61B 5/7264 |

(Continued)

FOREIGN PATENT DOCUMENTS

| | | |
|---|---|---|
| CN | 202729525 U | 2/2013 |
| CN | 106859875 A | 6/2017 |
| CN | 108814826 A | 11/2018 |

(Continued)

OTHER PUBLICATIONS

Extended European Search Report from European Patent Office dated Jan. 24, 2022 in related International Application No. 21197115.5 (9 pages total).

(Continued)

*Primary Examiner* — Michael A Berns
(74) *Attorney, Agent, or Firm* — DINSMORE & SHOHL LLP (57) ABSTRACT

A wheelchair system comprises a wheelchair comprising a seat, one or more first sensors disposed on or within the seat, one or more second sensors configured to communicate with the one or more first sensors and configured to be associated with a user to determine if the user is falling out of the wheelchair, wherein, upon detection that the user is falling out of the wheelchair, the wheelchair is configured to automatically stop.

20 Claims, 4 Drawing Sheets

(56) References Cited

U.S. PATENT DOCUMENTS

2022/0079822 A1\* 3/2022 Moore ................ A61G 5/1005

FOREIGN PATENT DOCUMENTS

| CN | 110693650 | A | 1/2020 |
|----|-----------|---|--------|
| KR | 20130107487 | A | 10/2013 |
| WO | 2019018167 | A1 | 1/2019 |

OTHER PUBLICATIONS

Rima Sabina Aouf, "Five Designers Awarded $500,000 Each to Develop Mobility Devices for Lower-Limb Paralysis", Jan. 7, 2019, 14 pages, https://www.dezeen.com/2019/01/07/mobility-unlimited-challenge-shortlist-finalists-paralysis/.

\* cited by examiner

WHEELCHAIR SYSTEMS WITH EMERGENCY STOP FEATURES

TECHNICAL FIELD

Embodiments described herein generally relate to wheelchairs and, more specifically, to a wheelchair system with emergency stop features.

BACKGROUND

Wheelchairs are often used as a mobility device for individuals with mobility impairments. An individual may sit in a wheelchair, such as a power wheelchair, and use one or more controls to direct the movement of the wheelchair. The wheelchair may be moved by motors or other actuators located on the wheelchair. As such, the wheelchair may be used by the individual to navigate an environment.

However, individuals that use a wheelchair may have limited physical capacity. As such, as a wheelchair moves through an environment, a user sitting in the wheelchair may fall out of the wheelchair, which may cause injury to the user. Accordingly, there is a need for a wheelchair that can inhibit a user from falling out of the wheelchair.

SUMMARY

In one embodiment, a wheelchair system includes a wheelchair comprising a seat, one or more first sensors disposed on or within the seat, and one or more second sensors configured to communicate with the one or more first sensors and configured to be associated with a user to determine if the user is falling out of the wheelchair. Upon detection that the user is falling out of the wheelchair, the wheelchair is configured to automatically stop.

In another embodiment, a wheelchair system includes a wheelchair comprising a seat portion and a back portion, and one or more first sensors disposed on or within the seat portion or the back portion, a master controller, a seat adjustment actuator, and one or more second sensors configured to communicate with the one or more first sensors and the master controller and configured to be associated with a user to determine movement of the user in the wheelchair. Upon detection of movement of the user in the wheelchair, the master controller is configured to cause the seat adjustment actuator to adjust the seat portion or the back portion based on the movement of the user.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Embodiments of the present disclosure generally relate to wheelchair systems with emergency stop features. A wheelchair, such as a power wheelchair, may contain one or more sensors that may be paired with sensors attached to or embedded in clothing of a user. When the user uses the wheelchair, the paired sensors are able to determine if the user is falling out of the wheelchair. When the user begins to fall out of the wheelchair, the wheelchair may automatically stop to prevent injury to the user. In some embodiments, the wheelchair may determine the direction that the user is falling out of the wheelchair and may adjust the seating position of the wheelchair accordingly to inhibit or prevent the user from falling out of the wheelchair.

Figure 1:
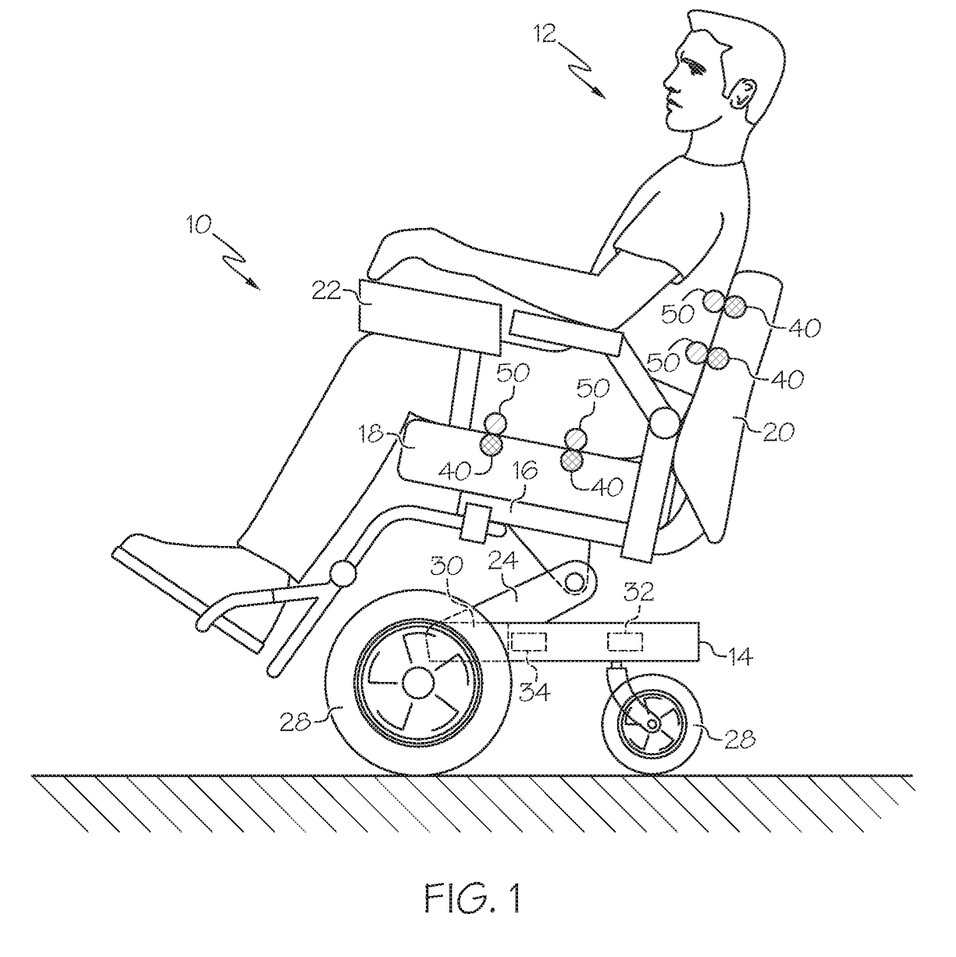
FIG. 1 schematically depicts an illustrative wheelchair according to one or more embodiments shown or described herein.

Referring to FIG. 1, a schematic depiction of a wheelchair 10 is provided. The wheelchair 10 may be a generally recognized wheelchair and, in some embodiments, may be a powered wheelchair that includes motorized components that allow a user 12 to electronically control movement of the wheelchair 10. In some embodiments, the wheelchair 10 may be an autonomously controlled wheelchair, wherein movement of the wheelchair is controlled without direct control by the user 12. Various components of the wheelchair 10 should be understood and are not described in further detail herein. In some embodiments, the wheelchair 10 may include a power base portion 14, a frame 16, a seat defined by a seat portion 18 and a back portion 20 supported by the frame 16, which in turn is supported by the power base portion 14. Thus, the frame 16 is generally positioned below the seat portion 18 in a vertical direction and the power base portion 14 is generally positioned below the frame 16 in a vertical direction. In some embodiments, the power base portion 14 may raise, tilt, or otherwise move the frame 16 and subsequently the seat portion 18. For example, the power base portion 14 may cause a seat adjustment actuator 24 to raise, lower, tilt, or otherwise move the frame 16, the seat portion 18, and/or the back portion 20. The seat adjustment actuator 24 may comprise a motor or any other suitable mechanism to move the frame 16, the seat portion 18, and/or the back portion 20. In some embodiments, other mechanisms may be used to adjust the frame 16 and the seat portion 18. The frame 16, the seat portion 18, and the back portion 20 are generally configured to support a user 12 when the user 12 is seated in the wheelchair 10.

In embodiments, a control member 22 may be coupled to the wheelchair 10. The control member 22 may be utilized by the user 12 as an input device to the wheelchair 10. The control member 22 may be used to input instructions to the wheelchair 10, such as movement instructions. The control member 22 may comprise a touch screen, a joystick, buttons, switches, voice controls, breath controls, and/or the like to receive inputs from the user 12. The control member 22 may be communicatively coupled to the power base portion 14, including various components thereof, to transmit signals to the power base portion 14 to cause the wheelchair 10 to respond according to the inputs received by the control member 22.

The power base portion 14 may include, but is not limited to, a plurality of wheels 28, a motor 30, a battery 32, and a master controller 34. The master controller 34 may be an electronic control unit and may generally be a control device that controls the wheelchair 10 and/or one or more components thereof. As such, the master controller 34 may be communicatively coupled to the various components of the wheelchair 10 such that one or more control signals can be transmitted from the master controller 34 to the various components as described in greater detail herein. The master controller 34 is described in further detail below, in connection with FIG. 3.

The wheelchair 10 may also comprise one or more sensors 40. The sensors 40 may communicate with paired sensors 50 that may be embedded in clothing of the user 12 to indicate the presence and/or position of the user 12 in the wheelchair 10, as explained in further detail below. The sensors 40 may comprise magnetic sensors, proximity sensors, RFID sensors, or any other sensor capable of indicating the presence and/or position of the user 12 with respect to the wheelchair 10. In the example of FIG. 1, two sensors 40 are attached to the back portion 20 and two sensors 40 are attached to the seat portion 18. However, it should be understood that the wheelchair 10 may include any number of sensors 40 at various locations on the wheelchair 10. The sensors 40 may be communicatively coupled to the master controller 34, as explained in further detail below.

Figure 2A:
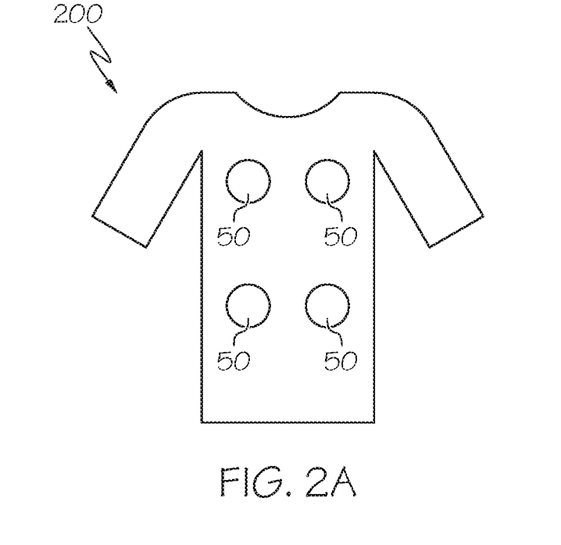
FIG. 2A depicts an exemplary shirt comprising sensors according to one or more embodiments shown or described herein.
Figure 2B:
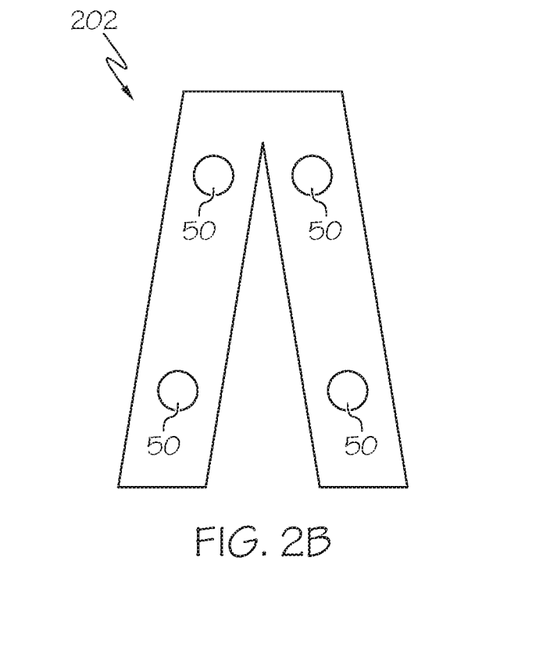
FIG. 2B depicts an exemplary pair of pants comprising sensors according to one or more embodiments shown or described herein.

One or more sensors 50 may be attached to or embedded in clothing worn by the user 12. The sensors 50 may be used to indicate the position and/or presence of the user 12 in the wheelchair 10 (e.g., the presence of the user 12 on the seat portion 18). The sensors 50 may comprise magnetic sensors, proximity sensors, RFID sensors, or any other sensor capable of indicating the presence and/or position of the user 12 with respect to the wheelchair 10. In the example of FIG. 1, two sensors 50 are attached to a shirt worn by the user 12 and two sensors 50 are attached to pants worn by the user 12. However, it should be understood that any number of sensors 50 may be provided in or on any portion of the clothing of the user 12. FIG. 2A shows an example shirt 200 having four sensors 50 attached thereto and FIG. 2B shows an example pair of pants 202 having four sensors 50 attached thereto. In some embodiments, the sensors 50 may be communicatively coupled to the master controller 34, as explained in further detail below.

The sensors 50 may be sewn into, clipped onto, or otherwise attached to the clothing of the user 12 by any other method. In some embodiments, the sensors 50 may be clipped to the wheelchair 10 (e.g., to the seat portion 18 and/or the back portion 20). In some embodiments, the sensors 50 may be embedded in wearable electronic devices such as a smart watch, or in a portable electronic device such as a smart phone carried by the user 12.

Each of the sensors 50 may be paired to one of the sensors 40. For example, as shown in FIG. 1, the two sensors 50 attached to the user 12's shirt may be paired to the two sensors 40 in the back portion 20 of the wheelchair 10 and the two sensors 50 in the user 12's pants may be paired to the two sensors 40 in the seat portion 18 of the wheelchair 10. The sensors 50 may be aligned with the sensors 40 when the user 12 is properly seated in the wheelchair 10, as shown in FIG. 1. Thus, each of the sensors 40 may determine a proximity to a paired sensor 50.

If the user 12 begins to slide or fall out of or otherwise move in the wheelchair 10, this movement may be detected by the sensors 40, 50. For example, in embodiments, the distance between the sensors 50 and the paired sensors 40 may increase as the user 12 begins to fall out of the wheelchair 10. In some embodiments, the sensors 40, 50 may detect a rate of change of the distance between the sensors. This rate of change may be used to determine how fast the user 12 is falling out of the wheelchair 10. In other embodiments, other data collected by the sensors 40, 50 may be used to determine a position or movement of the user 12 in the wheelchair 10. As such, the data collected by the sensors 40, 50 may be transmitted to the master controller 34. The master controller 34 may then adjust the movement and/or the seating of the wheelchair 10 accordingly, as discussed in further detail below.

Figure 3:
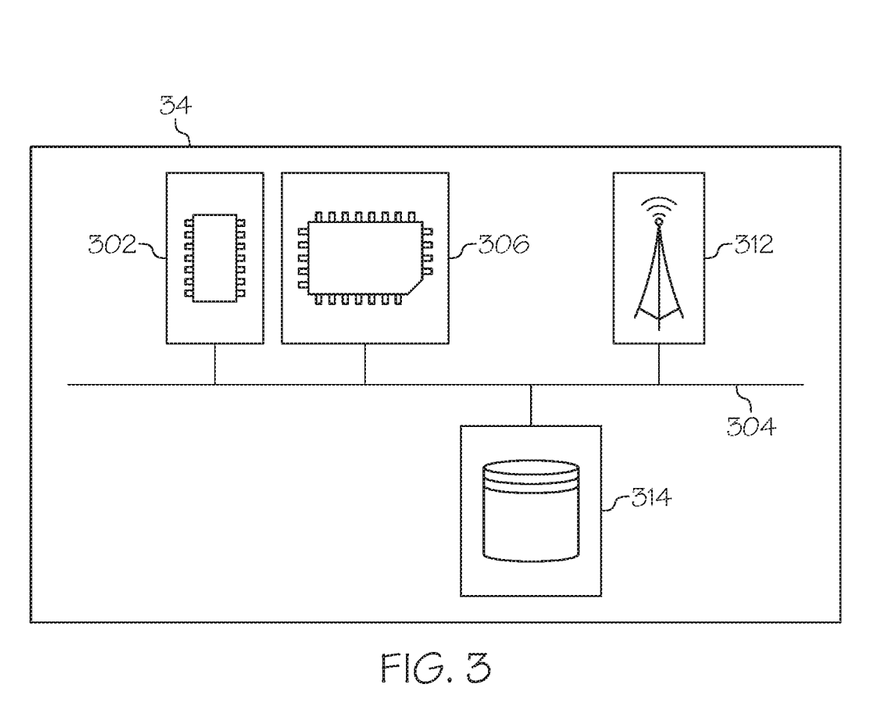
FIG. 3 depicts a schematic diagram of an example master controller of the wheelchair of FIG. 1, according to one or more embodiments shown and described herein.

FIG. 3 depicts an example master controller 34 included in the wheelchair 10 of FIG. 1. The master controller 34 includes one or more processors 302, a communication path 304, one or more memory modules 306, network interface hardware 312, and a data storage component 314, the details of which will be set forth in the following paragraphs. It should be understood that the master controller 34 of FIG. 3 is provided for illustrative purposes only, and that other master controllers 34 comprising more, fewer, or different components may be utilized.

Each of the one or more processors 302 may be any device capable of executing machine readable and executable instructions. Accordingly, each of the one or more processors 302 may be a controller, an integrated circuit, a microchip, a computer, or any other computing device. The one or more processors 302 are coupled to a communication path 304 that provides signal interconnectivity between various modules of the master controller 34. Accordingly, the communication path 304 may communicatively couple any number of processors 302 with one another, and allow the modules coupled to the communication path 304 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 304 may be formed from any medium that is capable of transmitting a signal such as, for example, conductive wires, conductive traces, optical waveguides, or the like. In some embodiments, the communication path 304 may facilitate the transmission of wireless signals, such as WiFi, Bluetooth®, Near Field Communication (NFC) and the like. Moreover, the communication path 304 may be formed from a combination of mediums capable of transmitting signals. In one embodiment, the communication path 304 comprises a combination of conductive traces, conductive wires, connectors, and buses that cooperate to permit the transmission of electrical data signals to components such as processors, memories, sensors, input devices, output devices, and communication devices. Accordingly, the communication path 304 may comprise a bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The master controller 34 includes one or more memory modules 306 coupled to the communication path 304. The one or more memory modules 306 may comprise RAM, ROM, flash memories, hard drives, or any device capable of storing machine readable and executable instructions such that the machine readable and executable instructions can be accessed by the one or more processors 302. The machine readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable and executable instructions and stored on the one or more memory modules 306. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. The memory modules 306 of the master controller 34 200 are described in further detail below with respect to FIG. 4.

Still referring to FIG. 3, the master controller 34 200 comprises network interface hardware 312 for communicatively coupling the master controller 34 to the sensors 40, 50. The network interface hardware 312 can be communicatively coupled to the communication path 304 and can be any device capable of transmitting and/or receiving data via a network. Accordingly, the network interface hardware 312 can include a communication transceiver for sending and/or receiving any wired or wireless communication. For example, the network interface hardware 312 may include an antenna, a modem, LAN port, Wi-Fi card, WiMax card, mobile communications hardware, near-field communication hardware, satellite communication hardware and/or any wired or wireless hardware for communicating with other networks and/or devices. In one embodiment, the network interface hardware 312 includes hardware configured to operate in accordance with the Bluetooth® wireless communication protocol. The network interface hardware 312 of the master controller 34 may receive data from the sensors 40, 50, as disclosed herein.

Still referring to FIG. 3, the master controller 34 comprises a data storage component 314. The data storage component 314 may store data that may be utilized by the memory modules 306 and/or other components of the master controller 34. For example, the data storage component 314 may store sensor data received from the sensors 40, 50. Other data that may be stored in the data storage component 214 is described throughout this disclosure.

Figure 4:
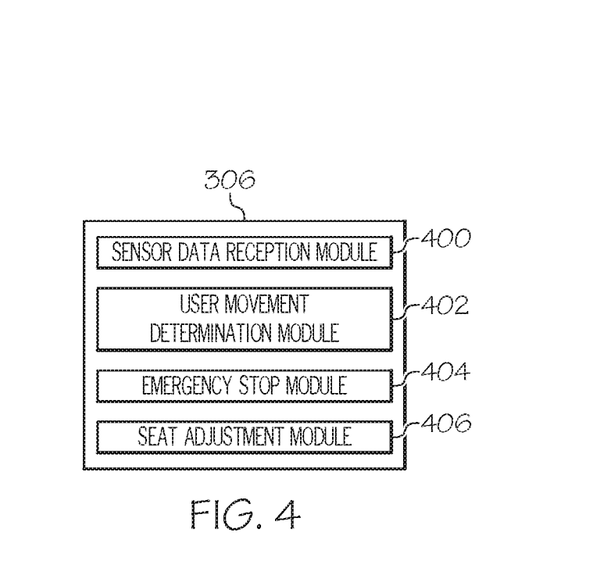
FIG. 4 depicts a schematic diagram of exemplary memory modules of the master controller of FIG. 3, according to one or more embodiments shown and described herein.

Now referring to FIG. 4, exemplary memory modules 306 of the master controller 34 are shown. The one or more memory modules 306 include a sensor data reception module 400, a user movement determination module 402, an emergency stop module 404, and a seat adjustment module 406. Each of the sensor data reception module 400, the user movement determination module 402, the emergency stop module 404, and the seat adjustment module 406 may be a program module in the form of operating systems, application program modules, and other program modules stored in the one or more memory modules 306. Such a program module may include, but is not limited to, routines, subroutines, programs, objects, components, data structures and the like for performing specific tasks or executing specific data types as will be described below.

The sensor data reception module 400 may receive data from the sensors 40 and/or 50. In the illustrated example, the sensor data reception module 400 receives data from only the sensors 40. However, in other examples, the sensor data reception module 400 may receive data from the sensors 50 in addition to or instead of from the sensors 40.

As the wheelchair 10 moves the user 12 around an environment, the sensors 40 and 50 may continually communicate with each other and collect data, which the master controller 34 may use to determine if the user 12 is properly seated in the wheelchair 10. If the sensors 40 detect that the user 12 is not properly seated in the wheelchair 10 (e.g., the user 12 is falling out of the seat portion 18), the sensors 40 and/or the sensors 50 may transmit a signal to the master controller 34. In other embodiments, the sensors 40 and/or 50 may continually transmit data to the master controller 34 and the master controller 34 may determine whether the user 12 is falling out of the wheelchair 10 based on the received data, as explained in further detail below.

For example, each of the paired sensors 40, 50 may transmit the distance between them to the master controller 34. In other examples, each of the sensors 50 may clip onto a corresponding sensor 40, and the sensors 40 may transmit a signal to the master controller 34 when one or the sensors 40 becomes unclipped from a paired sensor 50. In some examples, each of the sensors 40 may transit data to the master controller 34 indicating a relative position between the sensor 40 and a paired sensor 50. In some examples, when a sensor 50 is moving away from a paired sensor 40, the sensor 40 may transmit the rate at which the sensor 50 is moving away from the sensor 40 to the master controller 34. In other examples, the sensors 40 may transmit other data to the master controller 34. All such data transmitted from the sensor and/or the sensors 50 may be received by the sensor data reception module 400.

Referring still to FIG. 4, the user movement determination module 402 may determine movement and/or a position of the user 12 in the wheelchair 10 based on the data received by the sensor data reception module 400. The movement determination module 402 may determine a direction that the user 12 is moving in the wheelchair 10. The movement determination module 402 may also determine a rate of movement of the user 12 in the wheelchair 10. Based on the direction and/or the rate that the user 12 is moving in the wheelchair 10, the movement determination module 402 may determine if the user 12 is falling out of the wheelchair 10, using the techniques described herein.

In one example, the user movement determination module 402 may determine that the user 12 is falling out of the wheelchair 10 if a distance between a sensor 40 and a paired sensor 50 is greater than a predetermined threshold amount. In another example, the user movement determination module 402 may determine that the user 12 is falling out of the wheelchair 10 if a distance between a sensor 40 and a paired sensor 50 increases by more than a threshold amount. In other examples, the user movement determination module 402 may determine that the user 12 is falling out of the wheelchair 10 using other metrics based on the data received by the sensor data reception module 400. In some examples, the user movement determination module 402 may determine a rate at which the user 12 is falling out of the wheelchair 10 based on a rate of change between a relative position of one or more sensors 40 and paired sensors 50.

In some embodiments, the user movement determination module 402 may determine a direction that the user 12 moving, such as a direction that the user 12 is falling out of the wheelchair 10 based on data received by the sensor data reception module 400. For example, if one or more of the sensors 50 move away from a paired sensor 40 in a particular direction, the user movement determination module 402 may detect the direction that the sensors 50 are moving away from the sensors 40 and determine a direction that the user 12 is moving in the wheelchair 10 accordingly. For example, if a sensor 50 moves to the right of a paired sensor 40, the user movement determination module 402 may determine that the user 12 is moving to the right side of the wheelchair 10, and potentially falling out of the right side of the wheelchair 10.

Referring still to FIG. 4, the emergency stop module 404 may automatically stop the wheelchair 10 from moving (e.g., by shutting off the motor 30) based on movement of the user 12 in the wheelchair 10 determined by the user movement determination module 402. For example, the emergency stop module 404 may automatically stop the wheelchair 10 when the user movement determination module 402 determines that the user 12 is falling out of the wheelchair 10. This may allow for the user 12 to readjust his or her position in the wheelchair 10 or receive assistance without the wheelchair 10 continuing to move, which may cause the user 12 to completely fall out of the wheelchair 10 as the wheelchair 10 continues to move.

In some examples, the emergency stop module 404 may only stop the wheelchair 10 when the rate at which the user 12 is falling out of the wheelchair 10 is greater than a predetermined threshold. In other examples, the emergency stop module 404 may stop the wheelchair 10 when other metrics are met based on one or more determinations made by the user movement determination module 402.

The seat adjustment module 406 may cause the seat portion 18, the back portion 20, and/or other portions of the wheelchair 10 to be automatically adjusted based on movement of the user 12 in the wheelchair 10 determined by the user movement determination module 402. This may prevent or inhibit the user 12 from falling out of the wheelchair 10. The adjustments to the seating of the wheelchair 10 that may be caused by the seat adjustment module 406 may include tilting the back portion 20 forwards, backwards, or to one side, moving the seat portion 18 forwards, backwards or to the sides, or other adjustments. Specifically, the seat adjustment module 406 may cause the seat adjustment actuator 24 to adjust the seating of the wheelchair 10, as explained herein.

After the user movement determination module 402 determines a direction that the user 12 is moving in the wheelchair 10 (e.g., a direction that the user 12 is falling out of the wheelchair 10), the seat adjustment module 406 may adjust the seating of the wheelchair 10 based on the determined direction that the user 12 is moving or falling out of the wheelchair 10. For example, if the user movement determination module 402 determines that the user 12 is sliding forward out of the seat portion 18 of the wheelchair 10, the seat adjustment module 406 may cause the seat portion 18 to move forward to inhibit or prevent the user 12 from falling out of the wheelchair 10. If the user movement determination module 402 determines that the user 12 is sliding to the side of the seat portion 18 of the wheelchair 10, the seat adjustment module 406 may cause the seat portion 18 to move to the side to inhibit or prevent the user 12 from falling out of the wheelchair 10. In other examples, the seat adjustment module 406 may adjust the seating of the wheelchair 10 based on other determinations made by the user movement determination module 402, such as a position of the user 12 in the wheelchair 10 (e.g., a direction that the user 12 is leaning).

Figure 5:
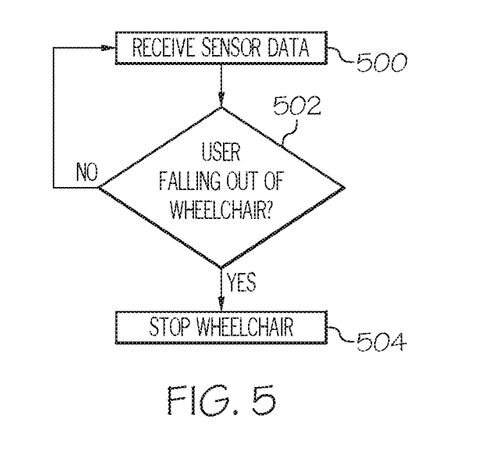
FIG. 5 depicts a flowchart of an illustrative method carried out by the wheelchair of FIG. 1 according to one or more embodiments shown or described herein.

Now referring to FIG. 5, a flowchart of an illustrative method of operation of the wheelchair 10 is depicted. At step 500, the sensor data reception module 400 receives data from one or more of the sensors 40 and/or 50. At step 502, the user movement determination module 402 determines whether the user 12 is falling out of the wheelchair 10 based on the data received by the sensor data reception module 400. If the user movement determination module 402 determines that the user 12 is not falling out of the wheelchair 10 ("No" at step 502), then control returns to step 500. If the user movement determination module 402 determines that the user 12 is falling out of the wheelchair 10 ("Yes" at step 502), then at step 504, the emergency stop module 404 stops the wheelchair 10 from moving.

Figure 6:
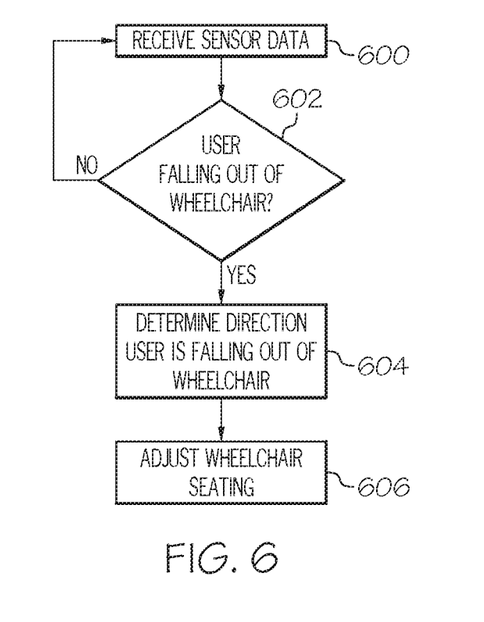
FIG. 6 depicts a flowchart of another illustrative method carried out by the wheelchair of FIG. 1 according to one or more embodiments shown and described herein.

Now referring to FIG. 6, a flowchart of another illustrative method of operation of the wheelchair 10 is depicted. At step 600, the sensor data reception module 400 receives data from one or more of the sensors 40 and/or 50. At step 602, the user movement determination module 402 determines whether the user 12 is falling out of the wheelchair 10 based on the data received by the sensor data reception module 400. If the user movement determination module 400 determines that the user 12 is not falling out of the wheelchair 10 ("No" at step 602), then control returns to step 600. If the user movement determination module 402 determines that the user 12 is falling out of the wheelchair 10 ("Yes" at step 602), then control passes to step 604.

At step 604, the user movement determination module 402 determines the direction that the user 12 is falling out of the wheelchair 10 based on the data received by the sensor data reception module 400. Then at step 606, the seat adjustment module 406 adjusts the position of the seat portion 18, the back portion 20, and/or other components of the wheelchair 10 based on the direction that the user 12 is falling out of the wheelchair 10. In embodiments, the seat adjustment module 406 adjusts the position of the seat portion 18, the back portion 20, and/or other components of the wheelchair 10 by transmitting an appropriate signal to the seat adjustment actuator 24.

It should now be understood that embodiments of the present disclosure are directed to wheelchairs having one or more sensors that communicate with one or more paired sensors attached to or embedded in the clothing of a user of the wheelchair. The paired sensors in the wheelchair and in the user's clothing may communicate with each other and/or with one or more other components in the wheelchair 10 to determine if the user is falling out of the wheelchair. When it is determined that the user is falling out of the wheelchair, the movement of the wheelchair automatically stops.

The sensors may communicate with each other and/or with other components in the wheelchair to determine movement or a position of the user in the wheelchair. The wheelchair may then automatically adjust a seating portion, a back portion, or other portions of the wheelchair to prevent or reduce the chances of the user falling out of the wheelchair.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A wheelchair system comprising:
 a wheelchair comprising a seat;
 one or more first sensors disposed on or within the seat;
 one or more second sensors configured to communicate with the one or more first sensors and configured to be associated with a user to determine if the user is falling out of the wheelchair;
 wherein, upon detection that the user is falling out of the wheelchair, the wheelchair is configured to automatically stop.

2. The wheelchair system of claim 1, wherein the one or more second sensors are configured to be attached to the user's clothing.

3. The wheelchair system of claim 1, wherein the one or more second sensors are configured to be embedded in the user's clothing.

4. The wheelchair system of claim 1, wherein each of the one or more first sensors is paired with one of the one or more second sensors.

5. The wheelchair system of claim 1, further comprising a master controller configured to receive data from the one or more first sensors and the one or more second sensors and determine if the user is falling out of the wheelchair based on the received data.

6. The wheelchair system of claim 5, wherein at least one of the one or more first sensors is configured to be clipped to one of the one or more second sensors, and the master controller determines that the user is falling out of the wheelchair when at least one of the one or more first sensors becomes unclipped from the one of the one or more second sensors.

7. The wheelchair system of claim 6, wherein, upon detection that the user is falling out of the wheelchair, the master controller is configured to stop the wheelchair by shutting off power to a motor of the wheelchair.

8. The wheelchair system of claim 6, wherein the data received by the master controller comprises a distance between each of the one or more first sensors and a corresponding one of the one or more second sensors, and the master controller is configured to cause the wheelchair to stop if the distance between any of the one or more first sensors and a corresponding one of the one or more second sensors is greater than a predetermined threshold.

9. The wheelchair system of claim 6, wherein the data received by the master controller comprises a distance between each of the one or more first sensors and a corresponding one of the one or more second sensors, and the master controller is configured to cause the wheelchair to stop if the distance between any of the one or more first sensors and a corresponding one of the one or more second sensors increases by an amount greater than a predetermined threshold.

10. A wheelchair system comprising:
 a wheelchair comprising a seat portion and a back portion;
 one or more first sensors disposed on or within the seat portion or the back portion;
 a master controller;
 a seat adjustment actuator; and
 one or more second sensors configured to communicate with the one or more first sensors and the master controller and configured to be associated with a user to determine movement of the user in the wheelchair;
 wherein, upon detection of movement of the user in the wheelchair, the master controller is configured to cause the seat adjustment actuator to adjust the seat portion or the back portion based on the movement of the user.

11. The wheelchair system of claim 10, wherein the master controller is configured to receive data from the one or more first sensors or the one or more second sensors to determine a position of the user in the wheelchair and to cause the seat adjustment actuator to adjust the seat portion or the back portion based on the position of the user.

12. The wheelchair system of claim 10, wherein:
 at least one of the one or more first sensors is attached to the seat portion of the wheelchair; and
 at least one of the one or more first sensors is attached to the back portion of the wheelchair.

13. The wheelchair system of claim 10, wherein the one or more first sensors are configured to communicate with the one or more second sensors to determine if the user is falling out of the wheelchair based on the movement of the user.

14. The wheelchair system of claim 10, wherein the master controller is further configured to:
 receive data from the one or more first sensors and the one or more second sensors; and
 determine the movement of the user based on the received data.

15. The wheelchair system of claim 14, wherein:
 each of the one or more first sensors is paired to a corresponding one of the one or more second sensors; and
 the data received by the master controller comprises a relative position between each of the one or more first sensors and a corresponding one of the one or more second sensors.

16. The wheelchair system of claim 14, wherein the master controller is configured to:
 determine whether the user is falling out of the wheelchair based on the movement of the user; and
 upon determination that the user is falling out of the wheelchair, stop the wheelchair.

17. The wheelchair system of claim 16, further comprising a motor;
 wherein, upon determination that the user is falling out of the wheelchair, the master controller is configured to stop the wheelchair by shutting off power to the motor.

18. The wheelchair system of claim 16 wherein:
 the data received by the master controller comprises a distance between each of the one or more first sensors and a corresponding one of the one or more second sensors; and
 the master controller is configured to cause the wheelchair to stop if the distance between any of the one or more first sensors and a corresponding one of the one or more second sensors is greater than a predetermined threshold.

19. The wheelchair system of claim 16, wherein:
 the data received by the master controller comprises a distance between each of the one or more first sensors and a corresponding one of the one or more second sensors; and
 the master controller is configured to cause the wheelchair to stop if the distance between any of the one or more first sensors and a corresponding one of the one or more second sensors increases by an amount greater than a predetermined threshold.

20. The wheelchair system of claim 16, wherein:
 the data received by the master controller comprises a rate of change between a distance between each of the one or more first sensors and a corresponding one of the one or more second sensors; and the master controller is configured to cause the wheelchair to stop if the rate of change between any of the one or more first sensors and a corresponding one of the one or more second sensors is greater than a predetermined threshold.

\* \* \* \* \*

UNITED STATES PATENT AND TRADEMARK OFFICE
CERTIFICATE OF CORRECTION

| | | |
|---|---|---|
| PATENT NO. | : 11,786,421 B2 | Page 1 of 1 |
| APPLICATION NO. | : 17/022657 | |
| DATED | : October 17, 2023 | |
| INVENTOR(S) | : Douglas A. Moore | |

It is certified that error appears in the above-identified patent and that said Letters Patent is hereby corrected as shown below:

In the Claims

In Column 10, Line(s) 45, Claim 18, after "claim 16", insert --,--.

Signed and Sealed this
Twenty-first Day of May, 2024

Katherine Kelly Vidal
*Director of the United States Patent and Trademark Office*